(12) United States Patent
Ohta et al.

(10) Patent No.: US 9,066,968 B2
(45) Date of Patent: Jun. 30, 2015

(54) FLUID FOR PERITONEAL DIALYSIS

(71) Applicant: HAYASHIBARA CO. LTD, Okayama (JP)

(72) Inventors: Hitomi Ohta, Okayama (JP); Toshiharu Hanaya, Okayama (JP); Shigeharu Fukuda, Okayama (JP); Yoshikatsu Miwa, Okayama (JP); Toshio Miyake, Okayama (JP)

(73) Assignee: HAYASHIBARA CO. LTD, Okayama (JP)

( * ) Notice: Subject to any disclaimer, the term of this patent is extended or adjusted under 35 U.S.C. 154(b) by 0 days.

(21) Appl. No.: 14/169,518

(22) Filed: Jan. 31, 2014

(65) Prior Publication Data

US 2014/0148409 A1    May 29, 2014

Related U.S. Application Data

(62) Division of application No. 11/912,279, filed as application No. PCT/JP2006/307813 on Apr. 13, 2006, now abandoned.

(30) Foreign Application Priority Data

Apr. 20, 2005 (JP) ................. 2005-122995

(51) Int. Cl.
 A01N 43/04 (2006.01)
 A61K 31/70 (2006.01)
 A61K 31/715 (2006.01)
 A61K 31/716 (2006.01)
 A61K 31/702 (2006.01)
 A61K 31/7048 (2006.01)
 A61M 1/28 (2006.01)

(52) U.S. Cl.
 CPC ............. *A61K 31/716* (2013.01); *A61K 31/702* (2013.01); *A61K 31/7048* (2013.01); *A61M 1/287* (2013.01)

(58) Field of Classification Search
 CPC ............. A61K 31/716; A61K 31/702; A61K 31/7048; A61K 31/712; A61K 2300/00; A61M 1/287
 USPC .................................................... 514/61, 62
 See application file for complete search history.

(56) References Cited

U.S. PATENT DOCUMENTS

| | | | |
|---|---|---|---|
| 5,837,060 A | 11/1998 | Fouache nee Ducroquet et al. | |
| 6,156,797 A | 12/2000 | Kubo et al. | |
| 7,309,697 B2 | 12/2007 | Mukai et al. | |
| 2003/0194762 A1 | 10/2003 | Kubota et al. | |
| 2005/0020507 A1 | 1/2005 | Zieske et al. | |
| 2006/0210646 A1 | 9/2006 | Oku et al. | |

FOREIGN PATENT DOCUMENTS

| | | |
|---|---|---|
| EP | 1108434 A1 | 6/2001 |
| JP | 2-196724 A | 8/1990 |
| JP | 7-323084 A | 12/1995 |
| JP | 08-071146 A | 3/1996 |
| JP | 8-85701 A | 4/1996 |
| JP | 8-131541 A | 5/1996 |
| JP | 10-094598 A | 4/1998 |
| JP | 11-71273 A | 3/1999 |
| JP | 2005-095148 A | 4/2005 |
| WO | 94/14468 A1 | 7/1994 |
| WO | 02/10361 A1 | 2/2002 |
| WO | 2004/002467 A1 | 1/2004 |
| WO | 2005007171 | 1/2005 |
| WO | 2005021564 A | 3/2005 |

OTHER PUBLICATIONS

Sitter, T., Sauter, M. (2005) Impact of glucose in Peritoneal Dialysis: Saint or Sinner? Peritoneal Dialysis International, vol. 25, p. 415-425.*
International Search Report of PCT/JP2006/307813 dated Jul. 18, 2006.
Database WPI Week 200471 Thomson Scientfic London GB; AN 2004-721888 & JP 2004283571 A(SAKI A) Oct. 14, 2004 (XP-002597341).
Database WPI Week 200621 Thomson Scentfic ondon GB; AN 2006-203818 & WO 2006/022174 A1 (Hayashibara Seibutsu Kagaku KK) Mar. 2, 2006 (XP-002597342)
Supplementary European Search Report from corresponding European application No. EP06731749 dated Aug. 30, 2010.
Yamamoto, 1., Suga, S., Mitch, y., Tanaka, M., Mute, N. (1990) Antiscorbutic Activity of L-Ascorbic 2-Giucoside and its Availability as a Vitamin C Supplement in Normal Rats and Guinea Pigs. Journal of Pharmacobio-Dynamics, vol. 13, p. 688-695.
Reich, 1., Poon, C.Y., Sugita, E.T. (2000) "Tonicity, Osmoticity, Osmolarity" in Remington: The Science and Practice of Pharmacy, 20th Edition. Edited by Alfonso R. Gennaro. p. 246-256.

* cited by examiner

*Primary Examiner* — Scarlett Goon
(74) *Attorney, Agent, or Firm* — Browdy and Neimark, PLLC

(57) ABSTRACT

The present invention has an object to provide a fluid for peritoneal dialysis with satisfactory body fluid removability, high biocompatibility, and improved storage stability, and the object is attained by a fluid for peritoneal dialysis containing one or more saccharides selected from cyclonigerosylnigerose, cyclomaltosylmaltose, and L-ascorbic acid 2-glucoside.

5 Claims, No Drawings

FLUID FOR PERITONEAL DIALYSIS

TECHNICAL FIELD

The present invention relates to a fluid for peritoneal dialysis (i.e. peritoneal dialysis fluid; hereinafter abbreviated as "DF") that is applicable to a renal failure patient, particularly, a DF with an improved biocompatibility comprising one or more saccharides selected from the group consisting of cyclonigerosylnigerose, cyclomaltosylmaltose and L-ascorbic acid 2-glucoside.

BACKGROUND ART

Peritoneal dialysis is a therapy of removing or exchanging waste matters or body fluid in a peritoneal capillary vessel of a patient using a dialysis fluid injected into the peritoneal cavity, which is an important therapy for life-sustaining of a renal failure patient. Since the peritoneal dialysis does not always require huge apparatuses or facilities and many assists by doctors and nurses compared to hemodialysis that is another common therapy, it is widely accepted by patients who want rehabilitation or who have difficulty in going to medical care facilities because of their remote locations.

But peritoneal dialysis therapy has some following defects. First, most commercially available DFs contain glucose as an osmo-regulator, which leads to various problems. For example, glucose absorption into the patient body may result in elevated blood-sugar level, lipid metabolism abnormality and insufficient body fluid removal by peritoneal sclerosis. Second, there is another problem associated with the pH adjustment of the DF. Current DFs need to be regulated in an acidic condition to keep glucose stable at autoclaving, but acidifying fluids repetitively injected into the peritoneal cavity is unfavorable for the peritoneal cavity or the peritoneal mesothelial cells.

Third, it is known that 5-hydroxymethylfurfural that is a decomposition product of glucose is formed in a DF containing glucose by autoclaving or longtime storage even when the DF containing glucose is regulated in an acidic condition (q.v. Japanese Patent Kokai No. 71146/1996 for example). So, methods of reducing the formation of the decomposition product of glucose have been studied, for example, a method of removing the decomposition product from a DF and of changing the sterilization method or condition. However, a DF that containing no degradation product of glucose at all cannot be obtained as long as glucose exists in the DF as an osmo-regulator. Fourth, a DF containing glucose has a defect that the body fluid removability become lower with time because of the glucose absorption into the capillary vessel when the fluid is not exchanged for a long time after administered in the peritoneal cavity.

Therefore, methods of using a compound other than glucose as an osmo-regulator are proposed. For example, oligosaccharides, polysaccharides, amino acids, and glucose polymers i.e. starch hydrolyzates are quoted (for example, q.v. Japanese Patent Kokai No. 94598/1998 and Japanese Patent Kokai No. 85701/1996). But these are not yet in practical use because the above osmo-regulators cost a lot, their biosafety for longtime use is not known and they are easily decomposed. Also, methods of using an osmo-regulator containing an amino sugar or L-ascorbic acid is proposed (for example, q.v. Japanese Patent Kokai No. 71273/1999), but these compounds may lead to a problem of storage stability such as decomposition at autoclaving or brown matter production by the reaction with other ingredients. Therefore, development of a DF containing more beneficial osmo-regulator is desired.

DISCLOSURE OF INVENTION

An object of the present invention is to provide a DF having improved body-fluid removability, biocompatibility and storage stability.

The inventors of the present invention have dedicated to study to attain the above object and accomplished the present invention by finding out of an unexpected fact that a DF having improved body-fluid removability, biocompatibility and storage stability can be prepared by using one or more saccharides selected from the group consisting of cyclonigerosylnigerose, cyclomaltosylmaltose and L-ascorbic acid 2-glucoside as an osmo-regulator in the DF comprising electrolytes and osmo-regulators as the main ingredients.

The present invention can provide a DF having improved body-fluid removability, biocompatibility and storage stability, which brings the increased body fluid removal and elongated body fluid removing time. Since the decomposition of the ingredients such as glucose and the production of brown matters are inhibited by using the above saccharides, a DF having lowly biological injurious matter and improved storage stability can be obtained. Further, a DF with low damage to biological membranes and peritoneal mesothelial cells is obtained by using the above saccharides. Since glucose is not essential ingredient in the DF of the present invention and its amount can be determined accordingly, the DF can be used to a patient suffered from diseases such as diabetes.

BEST MODE FOR CARRYING OUT THE INVENTION

Cyclonigerosylnigerose used in the present invention is a cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} (throughout the specification, referred to as "cyclonigerosylnigerose", occasionally abbreviated as "CNN"), which was disclosed in International Patent application No. WO 02/10361 applied for by the same applicant of the present invention. Cyclomaltosylmaltose used in the present invention is a cyclic tetrasaccharide having a structure of cyclo{→6)-α-D-glucopyranosyl-(1→4)-α-D-glucopyranosyl-(1→6)-α-D-glucopyranosyl-(1→4)-α-D-glucopyranosyl-(1→} (throughout the specification, referred to as "cyclomaltosylmaltose", occasionally abbreviated as "CMM"), which was disclosed in Japanese Patent Kokai 95148/2005 applied for by the same applicant of the present invention. These two cyclic tetrasaccharides may be collectively referred to as "cyclotetrasaccharide". The cyclotetrasaccharides can be prepared by various methods such as fermentation, enzymatic synthesis or chemical synthesis. Considering economic efficiency, a method comprising a step of allowing cyclotetrasaccharide-forming enzyme to act on partial starch hydrolyzate is preferable, for example, disclosed in the above patent documents. By these methods, cyclotetrasaccharides can be made from starch that is a low-cost material in a high yield. The cyclotetrasaccharide of the present invention need not be highly purified and any form is acceptable, such as a composition containing other saccharides or cyclotetrasaccharide derivatives formed in the preparation process, its partially purified product, its highly purified product or a composition containing sugar alcohols produced by hydrogenation of reducing sugar formed in the preparation process.

However, for the administration into the peritoneal cavity, cyclotetrasaccharide with a purity of 98 w/w % or higher is preferred, a purity of 99 w/w % or higher is more preferable. For the administration, also the sterilized or pyrogen-free product is preferable.

L-Ascorbic acid 2-glucoside used in the present invention can be prepared by various methods such as fermentation, enzymatic synthesis or chemical synthesis. Considering economic efficiency, a method comprising a step of allowing a glucosyltransferase to act on a mixture of L-ascorbic acid and partial starch hydrolyzate, for example, disclosed in Japanese Patent Kokai No. 135992/1991 applied for by the same applicant of the present invention. By this method, L-ascorbic acid 2-glucoside can be made from partial starch hydrolyzate that is a low-cost material and L-ascorbic acid in a high yield. "AA2G" (an L-ascorbic acid 2-glucoside product commercialized by Hayashibara Biochemical Laboratories Inc., Okayama, Japan) can be used after sterilization and removal of pyrogen. The purity of L-ascorbic acid-2-glucoside used in the present invention is not restricted as long as the effect of the DF of the present invention is obtained, but for the administration into the peritoneal cavity, L-ascorbic acid-2-glucoside with a purity of 98 w/w % or higher is preferred, a purity of 99 w/w % or higher is more preferable. For the administration, the sterilized or pyrogen-free product is preferable.

The present invention relates to a DF containing one or more saccharides selected from the group consisting of CNN, CMM and L-ascorbic acid 2-glucoside as an osmo-regulator, which can regulate the osmotic pressure with the above ingredients at a low cost. The effect or time of body fluid removal can be altered or controlled by change of the kinds or the amounts of added osmo-regulators.

The osmotic pressure of the DF of the present invention is not restricted as long as the DF can remove the body fluid without serious biological disturbance. Usually, the amount and mixing ratio of one or more saccharides selected from the group consisting of CNN, CMM and L-ascorbic acid 2-glucoside, electrolyte and other ingredients are altered to adjust the osmotic pressure in a range of 282 to 820 mOsm/L, preferably in a range of 282 to 400 mOsm/L.

The DF of the present invention is preferable to be adjusted in pH 3 to 9, preferably in pH 5.0 to 7.5. By adjusting the pH of the DF in the above range, the damage to biological membranes and peritoneal mesothelial cells can be lowered. A physiologically applicable buffer, such as sodium lactate and sodium bicarbonate, is usable as the relevant buffer.

The DF of the present invention can be prepared by dissolving one or more saccharides selected from the group consisting of CNN, CMM and L-ascorbic acid 2-glucoside in water as an osmo-regulator and other physiologically acceptable ingredients that can be contained in the DF. The DF of the present invention also can be prepared by dissolving one or more saccharides selected from the group consisting of CNN, CMM and L-ascorbic acid 2-glucoside in an existing DF or replacing the partial or whole osmo-regulator in an current DF by one or more saccharides selected from the group consisting of CNN, CMM and L-ascorbic acid 2-glucoside. The additive amount of cyclotetrasaccharide and/or L-ascorbic acid 2-glucoside to the DF is determined as the osmotic pressure of the DF also containing electrolytes (inorganic salts) and other ingredients is regulated in the range described above. Usually, they are used in a range of 0.1% (w/v) to 35% (w/v), more preferably in a range of 0.5% (w/v) to 25% (w/v), on a dry solid basis (throughout the specification, "% (w/v)" is described as "%").

For adjustment of the body fluid removability, improvement of the storage stability, nutritional support or prevention and therapy of symptoms and complications caused by renal diseases or the dialysis, the DF of the present invention can be added with one or more members selected from the group consisting of various electrolytes, saccharides such as glucose, fructose, lactose, sucrose, α,α-trehalose, α,β-trehalose, β,β-trehalose, lactosucrose, maltooligosaccharides, cyclodextrins, syrups, maltodextrins, sugar alcohols such as mannitol, sorbitol, xylitol, maltotriitol, aminosugars such as glucosamine, acetyl glucosamine, galactosamine, non-reducing oligosaccharides or polysaccharides such as hydrogenated maltooligosaccharides and dextrins having α,α-trehalose structure within the molecule, pullulan, carrageenan, mucopolysaccharides such as chondroitin sulfate and hyaluronic acid and their salts, natural gums, synthetic polymers such as carboxymethylcellucose, water-soluble polymers such as collagen, gelatin, polypeptides in an amount without inhibition of the effects. It is preferable that the additive amount of the above electrolytes is determined as the ionic concentration is regulated close to that of a human body fluid. Usually, various electrolytes are admixed to give ionic concentrations of 120 mEq to 150 mEq of sodium ion, 0 mEq to 10 mEq of potassium ion, 3 mEq to 5 mEq of calcium ion, 0 mEq to 3 mEq of magnesium ion, 100 mEq to 120 mEq of chloride ion and 025 mEq to 40 mEq of bicarbonate ion. Phosphate ion or minor elements such as copper, zinc and lead can be added in addition to the above ions.

If necessary, the DF of the present invention can be advantageously added with one or more members selected from the group consisting of medicines such as antiinflammatory agent, antibacterial agent, antitumor agent, diuretic, antipyretic, analgesic, immunostimulator, cell cellstimulator, physiologically active substance, antioxidant, organic acids such as lactic acid, citric acid, glucronic acid, emulsifying agent, Vitamin P family such as lutin, hesperidin, naringin, Vitamins and its analogues such as Vitamin $B_1$, Vitamin $B_2$, Vitamin $B_6$, Vitamin $B_{12}$, L-ascorbic acid, Vitamin E and their derivatives, amino acids including amino derivatives of amino acid or N-acetyl amino acid, CoQ10 (coenzyme Q10), α-lipoic acid, L-carnitinne, based such as adenosine and its monophosphate, diphosphate and triphosphate.

The DF of the present invention can be prepared by incorporating the ingredients in a process of material input to end product or in an existing DF by a combinational method of one or more processes selected from the group consisting of dilute, concentration, drying, filtration, centrifugation, mixing, kneading, dissolution, melting, dispersion, suspension, emulsifying, immersion, permeation, spraying, inspersion, application, coating, solidification and grinding. The DF prepared by the above method is preferable to be packed into a bag made of flexible plastic such as poly(vinyl chloride) or ethylene-vinyl acetate or a glass vessel, and if necessary, sterilized by autoclaving, boiling or filtration. In a case of including an ingredient with low storage stability or an ingredient that tend to be denatured or decomposed by longtime coexistence with other ingredients, the DF can be prepared into two or more components and prepared by mixing them when used. Preparation of the DF by diluting the powdery products comprising the ingredients of the DF or its concentrated solution with water is feasible.

The DF of the present invention is applicable to a well-established peritoneal dialysis therapy without restriction. The dosage of the DF can be determined according to the condition of the subject patient, the purpose of the therapy or the degree of the loss of renal function without restriction. Usually, the DF is injected into the peritoneal cavity at a dose of 1 L to 2 L one or a few times a day and removed after a prescribed time to exchange and remove the accumulated body fluid and waste matters. It can be operated through a catheter indwelling in the peritoneal cavity by gravitation or with a pump by the patient or the carer at the patient's home, office, or while traveling. It can be operated also by an intermittent peritoneal dialysis or a mechanically-automated continuous cyclic peritoneal reflux method. The DF of the present invention can be used as a dialysate for hemodialysis, organ preservation fluid or wash fluid for peritoneal cavity, pleural cavity or organs.

Since cyclotetrasaccharide and L-ascrobic acid 2-glucoside have so highly inhibitive effects of radical production as to efficiently inhibit a disorder and its development with radical production, such as a irritation or cell disorder of peritonea, diaphragm or digestive system organs and irritating or festering wound at the access site of the catheter caused by the administration of the DF of the present invention, the DF is advantageous to biocompatibility.

The following experiments explain the present invention in details. In the following experiments, crystalline CNN pentahydrate prepared by the method of Preferred example 1 described later and crystalline CMM pentahydrate prepared by the method of Preferred example 2 described later were used as cyclic tetrasaccharide.

EXPERIMENT 1

Effects of Cyclic Tetrasaccharides and L-Ascrobic Acid 2-Glucoside on the Browning of DF According to the compositions described in Table 1, DFs comprising powdery crystalline CNN pentahydrate, powdery crystalline CMM pentahydrate, or L-ascrobic acid 2-glucoside (reagent grade, commercialized by Hayashibara Biochemical Laboratories Inc., Okayama, Japan) were prepared. These DFs were respectively placed in glass bottles, tightly sealed, and sterilized at 121° C. for 40 minutes. Successively, the browning of DFs and the formation of 5-hydroxymethyl-furfural were judged by macroscopically and the increase of absorbance at 284 nm. The results were also shown in Table 1. A DF comprising glucose, shown in Table 1, was used as a control.

TABLE 1

| | Composition (g/1000 mL) | | | | | |
|---|---|---|---|---|---|---|
| Ingredient | DF1 | DF2 | DF3 | DF4 | DF5 | Control |
| Sodium chloride | 5.38 | 5.38 | 5.38 | 5.38 | 5.38 | 5.38 |
| Sodium lactate | 7.4 | 7.4 | 7.4 | 7.4 | 7.4 | 7.4 |
| Calcium chloride dihydrate | 0.26 | 0.26 | 0.26 | 0.26 | 0.26 | 0.26 |
| Magnesium chloride hexahydrate | 0.05 | 0.05 | 0.05 | 0.05 | 0.05 | 0.05 |

TABLE 1-continued

| | Composition (g/1000 mL) | | | | | |
|---|---|---|---|---|---|---|
| Ingredient | DF1 | DF2 | DF3 | DF4 | DF5 | Control |
| CNN (d.s.b.*) | 25 | 0 | 0 | 12.5 | 0 | 0 |
| CMM (d.s.b.) | 0 | 25 | 0 | 0 | 12.5 | 0 |
| L-Ascorbic acid 2-glucoside | 0 | 0 | 25 | 12.5 | 12.5 | 0 |
| Glucose | 0 | 0 | 0 | 0 | 0 | 25 |
| Total volume (mL) | 1000 | 1000 | 1000 | 1000 | 1000 | 1000 |
| Browning | ND** | ND | ND | ND | ND | Detected |
| Formation of 5-hydroxymethyl furfural | ND | ND | ND | ND | ND | Detected |

*On a dry solid basis
**Not detected.

As is evident from the results in Table 1, all DFs, comprising cyclic tetrasaccharides, L-ascorbic acid 2-glucoside, and both cyclic tetrasaccharide and L-ascorbic acid, showed no browning and formation of 5-hydroxymethylfurfural after sterilization. On the contrary, DF comprising glucose, as a control, showed browning and formation of 5-hydroxymethyl-furfural, which is known as a substance harmful for living bodies. The results indicate that DFs comprising cyclic tetrasaccharides and/or L-ascorbic acid 2-glucoside exhibit outstanding stability and safety in comparison with that comprising glucose.

EXPERIMENT 2

Effect of a Cyclic Tetrasaccharide on the Body Fluid Removability of DF (1)

Experiments, examining the effects of a cyclic tetrasaccharide on the body fluid removability of DF, were carried out using dialysis tube as follows:

According to the compositions shown in Table 2, DFs comprising glucose or CNN are prepared, respectively. Into a dialysis tube (Molecular weight cut off: 15,000 daltons; diameter: 16 mm; length: 70 mm), 1.5 milliliters each of the DF was poured and sealed using a closer, and then put into one liter of a dialyzing solution, prepared by admixed sodium chloride and dextran (Molecular weight: 60,000 to 90,000 daltons; commercialized by Wako Pure Chemical Industries Ltd., Osaka, Japan) with purified water to give concentrations of 9 g/L and 6 g/L, respectively, for dialysis. The fluid volumes in the dialysis tube at one to 14 hours after the start of dialysis were examined by measuring the weight of the tube. In the experiment, three dialysis tubes were used for a kind of DF. The changes of fluid volumes in the dialysis tubes were measured by calculating the average of the results of three tubes expressed as relative values using each fluid volume at the start of dialysis as 100. The results were shown in Table 3.

TABLE 2

| | Composition (g/1000 mL) | | | | | | |
|---|---|---|---|---|---|---|---|
| Ingredient | DF1 | DF2 | DF3 | DF4 | DF5 | Control 1 | Control 2 |
| Sodium chloride | 4.48 | 4.48 | 4.48 | 4.48 | 4.48 | 4.48 | 4.48 |
| Sodium lactate | 5.35 | 5.35 | 5.35 | 5.35 | 5.35 | 5.35 | 5.3e5 |

TABLE 2-continued

| Ingredient | Composition (g/1000 mL) | | | | | | |
|---|---|---|---|---|---|---|---|
| | DF1 | DF2 | DF3 | DF4 | DF5 | Control 1 | Control 2 |
| Calcium chloride dihydrate | 0.26 | 0.26 | 0.26 | 0.26 | 0.26 | 0.26 | 0.26 |
| Magnesium chloride hexahydrate | 0.05 | 0.05 | 0.05 | 0.05 | 0.05 | 0.05 | 0.05 |
| CNN (d.s.b.*) | 10 | 30 | 75 | 150 | 300 | 0 | 0 |
| Glucose | 0 | 0 | 0 | 0 | 0 | 22.7 | 38.6 |
| Total volume (mL) | 1000 | 1000 | 1000 | 1000 | 1000 | 1000 | 1000 |
| Osmotic pressure (mOsm/L) | 282 | 329 | 388 | 513 | 821 | 392 | 489 |

*On a dry solid basis

TABLE 3

| Time elapsed from the start of dialysis (hour) | Increasing rate of DF volume (%) | | | | | | |
|---|---|---|---|---|---|---|---|
| | DF1 | DF2 | DF3 | DF4 | DF5 | Control 1 | Control 2 |
| 1 | 105 | 110 | 130 | 154 | 195 | 100 | 108 |
| 2 | 103 | 112 | 144 | 176 | 232 | 97 | 109 |
| 3 | 101 | 111 | 145 | 185 | 259 | 98 | 106 |
| 4 | 98 | 116 | 142 | 188 | 274 | 97 | 107 |
| 5 | 97 | 110 | 144 | 190 | 283 | 95 | 109 |
| 6 | 95 | 111 | 144 | 192 | 289 | 95 | 105 |
| 7 | 94 | 109 | 144 | 194 | 291 | 92 | 99 |
| 8 | 91 | 108 | 144 | 190 | 295 | 91 | 100 |
| 12 | 110 | 119 | 149 | 198 | 319 | 97 | 111 |
| 14 | 105 | 112 | 147 | 198 | 319 | 98 | 105 |

As is evident from the results in Table 3, in the cases of dialyzing DFs comprising 7.5% (w/v), 15% (w/v), or 30% (w/v) of CNN, DF3, DF4, or DF5, against one liter of dialyzing fluid, the fluidvolumes in dialysis tubes were increased in high percentages from one hour after of the start of dialysis in comparison with the case of a DF comprising 3.86% (w/v) of glucose (Control 2). Comparing the case of a DF comprising 2.27% (w/v) of glucose (Control 1) and that of a DF comprising 3% (w/v) of CNN (DF2), the increase of the fluid volume of DF2 showed higher percentage, but Control 1 and a DF comprising 1% (w/v) of CNN (DF1) showed no difference in the increase percentage of the fluid volume. Comparing the fluid volume in dialysis tubes among DFs comprising CNN, the increase percentage of the fluid volume was dependent to the amount of CNN comprised in DFs. A DF comprising 7.5% (w/v) of CNN (DF3), showing a lower osmotic pressure than a DF comprising 3.86% (w/v) of glucose (Control 2), and a DF comprising 15% (w/v) of CNN (DF4), showing almost equal osmotic pressure with Control 2, showed the higher increase percentage of the fluid volume in dialysis tubes than the case of Control 2. The results indicate that CNN exhibits better body fluid removability than glucose. In the case of using CMM, prepared by the method of "Preferred example 2 of preparation" described later, for the similar experiment instead of CNN in Table 2, almost the same results were obtained. Therefore, the results of the cases of using CNN are shown in Table 2 and those of the cases of using CMM are omitted.

EXPERIMENT 3

Effects of Cyclic Tetrasaccharides on the Body Fluid Removability of DF (2)

Experiments, examining the effects of a cyclic tetrasaccharide on the body fluid removability of DF, were carried out using rats as follows:

Into the electrolyte solution with a concentration described in Table2, CNN, CMM or L-ascorbic acid 2-glucoside was dissolved, and DFs comprising 7.5% (w/v) of CNN (DF1), 7.5% (w/v) of CMM (DF2), or 6.7% (w/v) of L-ascorbic acid 2-glucoside (DF3) were prepared, respectively. As a control, glucose was dissolved into the same electrolyte solution to give a concentration of 3.86%, on a dry solid basis, to make into a DF (Control). Successively, 10 milliliters each of DFs was administrated to peritoneal cavity of CD(SD)IGF rat (age in 7 to 8 weeks, male, weight: 256 to 317 grams, commercialized by Charles River Laboratories Japan, Inc., Kanagawa, Japan), pre-fasted for four hours and anesthetized by ether, using a 10 ml-capacity injection syringe with a 21-gauge needle. Rats were killed with anesthesia using ether after the administration of 2, 4, 6, or 14 hours. Then, the trapped fluid in the peritoneal cavity was collected using a 10 ml-capacity injection syringe with a 19-gauge needle, and the volume of the fluid was measured. Based on the fluid volumes, the increase of fluid volume was expressed as relative values using the fluid volume of Control, collected just after the administration, as 100, and were in Table 4. In the experiment, three rats were used at each measuring time. The average volume of DFs collected just after the administration in the peritoneal cavity was 9.4 milliliters.

TABLE 4

| Time elapsed from the start of dialysis (hour) | Increasing rate of DF volume injected into the peritoneal cavity (%) | | | |
|---|---|---|---|---|
| | DF1 | DF2 | DF3 | Control |
| 2 | 172 | 175 | 169 | 160 |
| 4 | 198 | 197 | 195 | 188 |
| 6 | 199 | 196 | 194 | 166 |
| 14 | 162 | 163 | 159 | 131 |

As is evident from the result in Table 4, in the cases of administrating DFs comprising CNN, CMM, and L-ascorbic acid 2-glucoside (DF1, DF2, and DF3) to peritoneal cavity, the fluid volumes of the trapped fluids in peritoneal cavities reached the maximum increase percentage (198%, 197%, and 195%), respectively, at four hours after the administration. Those increase percentages were kept at six hours after the administration and decreased at 14 hour after to 162%, 163%, and 159%, respectively. While, in the case of administrating a DF comprising glucose (Control) to peritoneal cavity, the fluid volume of the trapped fluid in peritoneal cavity was increased as in the cases of administrating DFs comprising CNN, CMM, and L-ascorbic acid 2-glucoside (DF1, DF2, and DF3). However, the increase percentage of Control was lower than DFs 1 to 3, and the increase percentage was changed to decrease at six hours after (166%), and it decreased to 131% at 14 hours after. The results indicate that DFs comprising CNN, CMM, or L-ascorbic acid 2-glucoside are better in the increase of the volume of removed body fluid than a DF comprising glucose when administrated to peritoneal cavity. Further, the results indicate that they exhibit better effect of extending period for body fluid removal than a DF comprising glucose.

The results of Experiments 1 to 3 indicate that DFs comprising cyclic tetrasaccharides and/or L-ascorbic acid 2-glucoside can be advantageously used as DFs because they are stable and show good body fluid removability which can be used to attain the increase of the volume of removed body fluid and the elongation of the period for body fluid removal.

PREFERRED EXAMPLE 1 OF PREPARATION

Preparation of Cyclonigerosylnigerose (CNN)

A corn starch was prepared into a about 20% (w/v) starch suspension, admixed with calcium carbonate to give a concentration of 0.1% (w/v), adjusted to pH 6.5, and admixed with 0.3%/g-starch of "THERMAMYL 60L" (an α-amylase commercialized by Novozymes Japan, Chiba, Japan) and then incubated at 95° C. for 15 min. After autoclaving at 120° C. for 20 min, the reaction mixture was cooled rapidly to about 35° C. to make into a liquefied starch solution with a DE (dextrose equivalent) of about 4. The liquefied starch solution was admixed with 0.2 ml/g-dry solid starch of an enzyme solution containing α-isomaltosylglucosaccharide-forming enzyme and α-isomaltosyl-transferring enzyme, originated from *Bacillus globisporus* C9, FERM BP-7143, disclosed in International Patent application No. WO 02/103611, and 10 units/g-dry solid starch of cyclomaltodextrin glucanotransferase (commercialized by Hayashibara Biochemical Laboratories Inc., Okayama, Japan) and followed by the enzymatic reaction at pH 6.0 and 35° C. for 48 hours. After heating to 95° C. for 30 min, the reaction mixture was cooled to about 50° C. and adjusted to pH 5.0. Then, the reaction mixture was admixed with 300 units/g-starch of "TRANSGLUCOSIDASE L (AMANO)" (an α-glucosidase commercialized by Amano Enzyme Inc., Aichi, Japan) and followed by the enzyme reaction for 24 hours. Further, the resulting reaction mixture was admixed with 30 units/g-starch of "GLUCOZYME" (a glucoamylase commercialized by Nagase ChemteX Corporation, Osaka, Japan) and followed by the enzyme reaction for 17 hours. After heating the reaction mixture to 95° C. and keeping for 30 min, it was cooled and filtrated. According to conventional manner, the resulting filtrate was decolored with activated charcoal, desalted and purified with ion exchangers in H– and OH– forms. Then, the purified solution was concentrated to give a syrup comprising CNN, with a concentration of 60%. The product contained, on a dry solid basis, 34.2% (w/w) of glucose, 62.7% (w/w) of CNN, and 3.1% (w/w) of other saccharides.

The syrup comprising CNN was subjected to a column chromatography using "AMBERLITE CR-1310" (Na-form), a strongly acidic cation-exchange resin (commercialized by Organo Corporation, Tokyo, Japan). The resin was packed into four jacketed stainless steel columns having a diameter of 5.4 cm, which were then cascaded in series to give a total gel bed depth of 20 m (gel bed depth of each column was 5 m). Under the conditions of keeping the inner column temperature at 60° C., the saccharide solution was fed to the columns in a volume of 5% (v/v) and fractionated by feeding to the columns hot water heated to 60° C. at an SV (space velocity) of 0.13 to obtain high CNN content fractions. While monitoring the saccharide composition of elute by HPLC, and then the high CNN content fractions were collected and purified to obtain a solution containing about 98% (w/w) CNN, on a dry solid basis. After concentrating the solution to give a concentration of about 70% (w/w), the concentrate was placed in a crystallizer. Then, a massecuite with a degree of crystallization of about 45% was obtained by adding about 2% of hydrous crystalline CNN as a seed crystal to the massecuite and cooling gradually. The massecuite was sprayed from a nozzle equipped on the top of a spraying tower at a pressure of 150 kg/cm². In the spraying step, the massecuite was simultaneously ventilated with 85° C. hot air sent from the top of spraying tower, and the resulting crystalline powder was collected on a metal wire netting conveyer provided on the basement of the spraying tower, and gradually moved out of the tower while a stream of 45° C. hot air was passing upwards through the metal wire netting. The resulting crystalline powder was injected in an aging tower and aged for 10 hours to complete the crystallization and drying. Thus, a powdery crystalline CNN pentahydrate with a purity of 98% or higher was obtained. The product is not hydrolyzed by enzymes in peritoneal cavity when used as an osmo-regulator for DF. Compared with DFs prepared by using glucose or oligosaccharides, a DF prepared using the product can be used to control the change of osmotic pressure in a small range. Therefore, the product can be advantageously used as an osmo-regulator.

PREFERRED EXAMPLE 2 OF PREPARATION

Preparation of Cyclomaltosylmaltose (CMM)

A liquid culture medium consisting of 1.5% (w/v) of "PINE-DEX #4" (a partial starch hydrolyzate commercialized by Matsutani Chemical Industries Co., Ltd., Hyogo, Japan), 0.5% (w/v) of "POLYPEPTONE" (a yeast extract commercialized by Nihon Pharmaceutical Co., Ltd., Tokyo, Japan), 0.1% (w/v) of "YEAST EXTRACT S" (a yeast extract commercialized by Nihon Pharmaceutical Co., Ltd., Tokyo, Japan), 0.1% (w/v) of dipotassium phosphate, 0.06% (w/v) of sodium phosphate dihydrate, 0.05% (w/v) of magnesium sulfate heptahydrate, 0.3% (w/v) of calcium carbonate, and water was prepared and inoculated with *Arthrobacter globiformis* M6, FERM BP-8448, disclosed in Japanese Patent Kokai No. 95,148/2005, and followed the cultivation under rotary-shaking conditions at 27° C. and 230 rpm for 120 hours. After completion of the culture, the culture supernatant was obtained by centrifuging at 8,000 rpm for 20 minutes the culture broth to remove cells. The resulting culture supernatant was used as an enzyme preparation and admixed with 50 mM acetate buffer containing 2% (w/v) of soluble starch and 2 mM of calcium chloride and followed by the reaction at 40° C. for 24 hours. The reaction was stopped by heating at about 100° C. for 10 minutes.

Successively, the above reaction mixture was adjusted to pH 5.0 using hydrochloric acid, then admixed with 4,000 units/g-dry solid of "TRANSGLUCOSIDASE-L AMANO" (an α-glucosidase commercialized Amano Enzyme Inc., Aichi, Japan) and 250 units/g-dry solid of glucoamylase (commercialized by Nagase ChemteX Corporation, Osaka, Japan) and followed by the reaction at 50° C. for 16 hours. After completion of the reaction, the reaction was stopped by heating at about 100° C. for 10 min. Then, the pH of the reaction mixture was adjusted to 12 by adding sodium hydroxide, and the resulting mixture was incubated at 98° C. for one hour to decompose reducing sugars. After removing insoluble substances from the reaction mixture by filtration, the resulting filtrate was decolored and desalted using "DIAION SK-1B" (an ion exchange resin commercialized by Mitsubishi Chemical Corporation, Tokyo, Japan) and "IRA 411" (an anion exchange resin commercialized by Organo Corporation, Tokyo, Japan). The resulting solution was filtrated, concentrated using an evaporator, and dried in vacuo to obtain a powdery crystalline CMM pentahydrate with a purity of 98% or higher. The product is not hydrolyzed by enzymes in peritoneal cavity when used as an osmo-regulator for DF. Compared with DFs prepared by using glucose or oligosaccharides, a DF prepared using the product can be used to control the change of osmotic pressure in a small range. Therefore, the product can be advantageously used as an osmo-regulator.

The following examples explain the present invention in more details, however, the present invention is not restricted by them.

Example 1

In distilled water were dissolved 9.5 g of powdery crystalline CNN pentahydrate, prepared by the method in Preferred example 1, 0.567 g of sodium chloride, 3.92 g of sodium lactate, 0.294 g of calcium chloride, and 0.103 g of magnesium chloride, and the solution was adjusted to a pH of about 7.5 with 0.294 g of sodium hydroxide and volume up to 1,000 ml with distilled water. The resulting solution was filtered with a 0.2 μm membrane filter, injected into a bag made of poly(vinyl chloride) resin (PVC), and autoclaved at 121° C. for 20 min.

Macroscopic observation on the coloration of the autoclaved solution confirmed that it had no coloration and also confirmed that, when measured for absorbance at a wavelength of 284 nm, it gave no increment in absorbance at the wavelength compared with that of the solution before autoclaving and formed no 5-hydroxymethylfurfurals. The product is a DF with improved storage stability and biocompatibility. The product can be also used as a dialysate for hemodialysis. The above-identified sodium lactate can be replaced with other buffer agent (sodium bicarbonate, etc.).

Example 2

In distilled water were dissolved 9.5 g of powdery crystalline CNN pentahydrate, prepared by the method in Preferred example 2, 0.1 g of glucose, 0.567 g of sodium chloride, 3.92 g of sodium lactate, 0.294 g of calcium chloride, and 0.103 g of magnesium chloride, and the solution was adjusted to a pH of about 7.5 with 0.294 g of sodium hydroxide and volume up to 1,000 ml with distilled water. The resulting solution was filtered with a 0.2 μm membrane filter, injected into a PVC bag, and autoclaved at 121° C. for 20 min.

Macroscopic observation on the coloration of the autoclaved solution confirmed that it had no coloration and also confirmed that, when measured for absorbance at a wavelength of 284 nm, it gave no increment in absorbance at the wavelength compared with that of the solution before autoclaving and formed no 5-hydroxymethylfurfurals. The product is a DF with improved storage stability and biocompatibility. The product can be also used as a dialysate for hemodialysis and a preservation fluid or a washing fluid for organs. The above-identified sodium lactate can be replaced with other buffer agent (sodium bicarbonate, etc.).

Example 3

Four grams of a commercially available L-ascorbic acid 2-glucoside (a reagent grade specimen, commercialized by Hayashibara Biochemical Laboratories Inc., Okayama, Japan) which had been treated with activated charcoal and membrane filtered with a 0.2 μm membrane filter to remove pyrogens and microorganisms, 0.567 g of sodium chloride, 3.92 g of sodium lactate, 0.294 g of calcium chloride, and 0.103 g of magnesium chloride, and the solution was adjusted to a pH of about 6.5 with an adequate amount of sodium hydroxide and volumed up to 1,000 ml with distilled water. The resulting solution was filtered with a 0.2 μm membrane filter, injected into a PVC bag, and autoclaved at 121° C. for 20 min.

The product is a DF with improved storage stability and biocompatibility. The product can be also used as a dialysate for hemodialysis.

Example 4

In distilled water were dissolved 4.6 g of powdery crystalline CNN pentahydrate, prepared by the method in Preferred example 1, 2.1 g of the L-ascorbic acid 2-glucoside free of pyrogen and microorganisms prepared in Example 3, 0.567 g of sodium chloride, 3.92 g of sodium lactate, 0.294 g of calcium chloride, and 0.103 g of magnesium chloride, and the solution was adjusted to a pH of about 7.5 with an adequate amount of sodium hydroxide and volumed up to 1,000 ml with distilled water. The resulting solution was filtered with a 0.2 μm membrane filter, injected into a PVC bag, and autoclaved at 121° C. for 20 min.

The product is a DF with improved storage stability and biocompatibility. The product can be also used as a dialysate for hemodialysis. The above-identified sodium lactate can be replaced with other buffer agent (sodium bicarbonate, etc.)

INDUSTRIAL APPLICABILITY

As described above, the present invention was made based on a complete self-finding that a DF containing one or more saccharides selected from CNN, CMM, and L-ascorbic acid 2-glucoside has distinct functions of satisfactory body fluid removability, high biocompatibility, and improved storage stability. The DF of the present invention can be used easily and comfortably as one for humans without fear of causing serious side effect. The present invention with such outstanding distinct functions and effects is a significant invention that will greatly contribute to this art.

The invention claimed is:

1. A method for administering peritoneal dialysis therapy to a patient in need thereof, comprising a step of injecting a fluid into the peritoneal cavity of the patient, said fluid being free of glucose and comprising sodium chloride, calcium chloride, and magnesium chloride along with sodium lactate or sodium bicarbonate in an effective amount sufficient for regulating the ionic concentration of said fluid such that it is close to that of a human body fluid and, as an effective ingredient, cyclo{→6)-α-D-glucopyranosyl-(1→3)-α-D-glucopyranosyl-(1→6)-α-D-glucopyranosyl-(1→3)-α-D-glucopyranosyl-(1→}, cyclo{→6)-α-D-glucopyranosyl-(1→4)-α-D-glucopyranosyl-(1→6)-α-D-glucopyranosyl-(1→4)-α-D-glucopyranosyl-(1→}, or a mixture thereof, in an effective amount sufficient for improving body-fluid removability, biocompatibility, and storage stability of said fluid.

2. The method of claim 1, wherein said fluid contains L-ascorbic acid 2-glucoside.

3. The method of claim 1, wherein said fluid contains said cyclo{→6)-α-D-glucopyranosyl-(1→3)-α-D-glucopyranosyl-(1→6)-α-D-glucopyranosyl-(1→3)-α-D-glucopyranosyl-(1→)} and said cyclo{→6)-α-D-glucopyranosyl-(1→4)-α-D-glucopyranosyl-(1→6)-α-D-glucopyranosyl-(1→4)-α-D-glucopyranosyl-(1→)} in a total amount of 0.1% w/v to 35% w/v.

4. The method of claim 1, wherein said fluid has an osmotic pressure of 282 mOsm/L to 820 mOsm/L.

5. The method of claim 1, wherein said fluid is adjusted to a pH of 3 to 9.

* * * * *